US006904319B2

(12) United States Patent
Seim et al.

(10) Patent No.: US 6,904,319 B2
(45) Date of Patent: Jun. 7, 2005

(54) METHOD AND APPARATUS FOR INHIBITING ATRIAL TACHYARRHYTHMIA THERAPY

(75) Inventors: Gary Seim, Minneapolis, MN (US); Lynn Elliott, Maple Grove, MN (US); Milton Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 151 days.

(21) Appl. No.: 09/827,775

(22) Filed: Apr. 6, 2001

(65) Prior Publication Data

US 2002/0147474 A1 Oct. 10, 2002

(51) Int. Cl.$^7$ ................................. A61N 1/18
(52) U.S. Cl. ........................................ 607/14
(58) Field of Search .................. 607/5, 9, 14; 600/515, 600/519

(56) References Cited

U.S. PATENT DOCUMENTS

| 5,205,283 | A | * | 4/1993 | Olson ............................ 607/4 |
| 5,411,530 | A | * | 5/1995 | Akhtar ......................... 607/14 |
| 5,846,263 | A | * | 12/1998 | Peterson et al. .............. 607/14 |
| 5,978,707 | A | | 11/1999 | Krig et al. |

* cited by examiner

Primary Examiner—Mark Bockelman
(74) Attorney, Agent, or Firm—Crawford Maunu PLLC (57) ABSTRACT

A system and method provides for inhibiting delivery of atrial therapy under certain conditions. Inhibiting delivery of atrial therapy involves developing atrial intervals and ventricular intervals from sensed atrial and ventricular events, respectively. An average atrial rate and an average ventricular rate is developed from a predetermined number of the atrial and ventricular intervals, respectively. Delivery of atrial therapy is inhibited if the average atrial rate fails to exceed the average ventricular rate by at least a predetermined factor.

42 Claims, 6 Drawing Sheets

METHOD AND APPARATUS FOR INHIBITING ATRIAL TACHYARRHYTHMIA THERAPY

FIELD OF THE INVENTION

The present invention relates generally to implantable medical devices and, more particularly, to implantable pacemakers and cardioverter-defibrillators for detecting and treating atrial tachyarrhythmias.

BACKGROUND OF THE INVENTION

Implantable cardioverter-defibrillators (ICDs) have been developed that employ detection algorithms capable of recognizing and treating atrial tachycardias and atrial fibrillation. In general, ICDs are designed to treat such tachycardias with antitachycardia pacing and low-energy cardioversion shocks in conjunction with back-up defibrillation therapy. These ICDs monitor the heart rate and the onset of the arrhythmia by sensing endocardial signals and determining when the heart is in need of either cardioversion to treat a given tachycardia or of defibrillation to treat a fibrillation condition.

Certain ICDs have been designed with dual chamber sensing capabilities to detect and analyze both ventricular and atrial endocardial signals. This increase in cardiac signal input to the ICD has provided an opportunity to determine the origin and the nature of atrial and ventricular tachyarrhythmia, and to reduce the frequency of inappropriate therapy being delivered to an implant patient.

However, while the combination of antitachycardia pacing with low and high energy shock delivery, as well as backup bradycardia pacing, in ICDs has expanded the number of clinical situations in which the devices may appropriately be employed, improved means of coordinating atrial rate information in a way that results in a system that effectively and efficiently treats atrial tachyarrhythmias is still desired.

For the reasons stated above, and for other reasons stated below which will become apparent to those skilled in the art upon reading the present specification, there is a need in the art for improved atrial arrhythmia detection and therapy techniques. There exists a further need for such techniques that provide for enhanced detection and treatment of atrial arrhythmias under conditions of varying cardiac activity, such as occurs during exercise. The present invention fulfills these and other needs.

SUMMARY OF THE INVENTION

The present invention is directed to a system and method for inhibiting delivery of atrial therapy under certain conditions. In accordance with an embodiment of the present invention, inhibiting delivery of atrial therapy involves developing atrial intervals and ventricular intervals from sensed atrial and ventricular events, respectively. An average atrial rate and an average ventricular rate is developed from a predetermined number of the atrial and ventricular intervals, respectively. Delivery of atrial therapy is inhibited if the average atrial rate fails to exceed the average ventricular rate by at least a predetermined factor.

According to another embodiment of the present invention, atrial intervals and ventricular intervals are developed from sensed atrial and ventricular events, respectively. A representative atrial interval rate and a representative ventricular interval rate is calculated using a predetermined number of the atrial and ventricular intervals, respectively. An average atrial rate and an average ventricular rate is calculated using the representative atrial and ventricular interval rates, respectively. Delivery of atrial therapy is inhibited if the average atrial rate fails to exceed the average ventricular rate by at least a predetermined factor.

Calculating the average atrial and ventricular rates may involve calculating the average atrial and ventricular rates on a beat per minute basis using the representative atrial and ventricular interval rates. The predetermined number of the atrial and ventricular intervals used to calculate the average atrial and ventricular rates may range between 4 and 60 of the most recent atrial and ventricular intervals, respectively, with a range between 5 and 20 representing a good sampling. In one embodiment, the predetermined number of atrial and ventricular intervals is about 10, respectively.

Delivery of atrial therapy, according to one embodiment of the present invention, is inhibited if the average atrial rate fails to exceed the average ventricular rate by a predetermined factor of at least 105 percent, such as between 105 and 125 percent, with 115 percent being a useful percentage. Atrial therapy may, for example, be inhibited if the average atrial rate fails to exceed the average ventricular rate by at least a predetermined factor ranging between 10 and 30 beats per minute, such as 20 beats per minute. After inhibiting atrial therapy, the capability to deliver atrial therapy may be subsequently enabled if the average atrial rate exceeds the average ventricular rate by at least the predetermined factor.

The representative atrial and ventricular interval rates may be computed by computing an average of a predetermined number of the atrial and ventricular intervals, respectively. The representative atrial and ventricular interval rates may also be computed by computing a median of a predetermined number of the atrial and ventricular intervals, respectively. The representative atrial and ventricular interval rates may alternatively be computed by computing a mean of a predetermined number of the atrial and ventricular intervals, respectively.

According to an alternative approach, average atrial and ventricular rates are developed based on a number of atrial and ventricular intervals respectively computed during a predetermined snapshot of time, rather than being based on a number n, m of the most recent atrial and ventricular intervals. The predetermined snapshot duration may range between about 2 seconds and 60 seconds, with a preferred range being between about 4 seconds and 30 seconds.

According to another embodiment of the present invention, a body implantable system includes at least one lead comprising atrial and ventricular electrodes. A detector, which is coupled to the lead, senses atrial events and ventricular events. A control circuit, coupled to the detector, calculates an average atrial rate and an average ventricular rate developed from a predetermined number of the atrial and ventricular intervals, respectively. The control circuit inhibits delivery of atrial therapy if the average atrial rate fails to exceed the average ventricular rate by at least a predetermined factor.

The control circuit may calculate the average atrial and ventricular rates on a beat per minute basis using an average, median or mean of the predetermined number of the atrial and ventricular intervals, respectively. The predetermined number of the atrial and ventricular intervals may range between 5 and 20 of the most recent atrial and ventricular intervals, respectively, with 10 representing a suitable predetermined factor.

The control circuit calculates the average atrial and ventricular rates preferably on a beat per minute basis using an average of the predetermined number of the atrial and ventricular intervals. The control circuit inhibits atrial therapy if the average atrial rate fails to exceed the average ventricular rate by at least a predetermined factor ranging between 10 and 30 beats per minute, such as 20 beats per minute. The predetermined factor may alternatively be expressed in terms of a ratio or percentage (e.g., such as a percentage between 105 percent and 125 percent). The control circuit enables the capability to deliver atrial therapy if the average atrial rate exceeds the average ventricular rate by at least the predetermined factor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Figure 1:
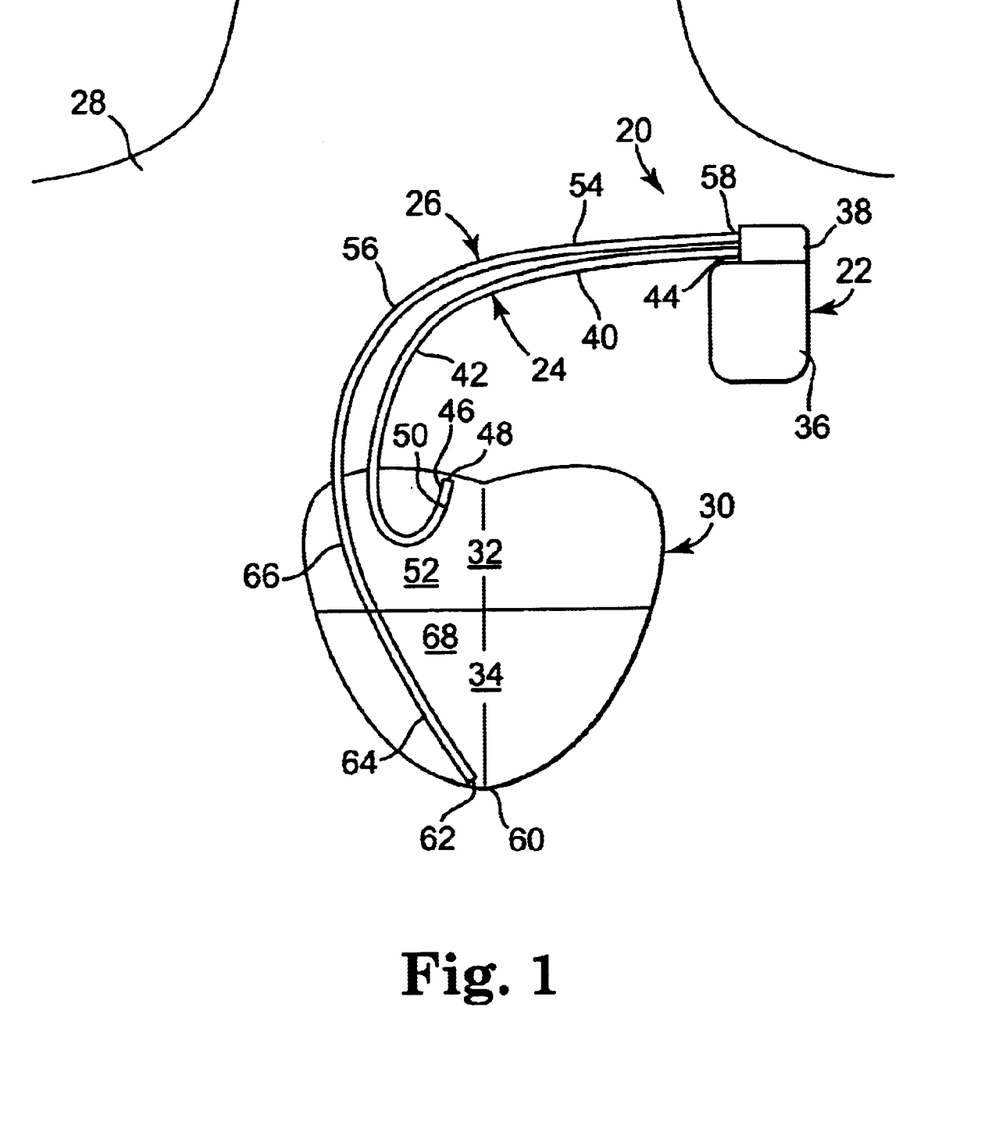
FIG. 1 is a depiction of an implantable medical device with which the atrial therapy inhibiting methodologies of the present invention may be practiced.

Referring now to the figures, and more particularly to FIG. 1, there is shown a body implantable system 20 that represents one of several types of systems with which the atrial therapy inhibiting methodologies of the present invention may be practiced. For example, the implantable pulse generator 22 may be representative of all or part of a pacemaker, defibrillator, cardioverter, cardiac monitor, or re-synchronization device. Accordingly, the atrial therapy inhibiting methodologies of the present invention may be practiced in a wide variety of implantable medical devices that sense cardiac activity.

The body implantable system 20 is shown to include an implantable pulse generator 22 coupled to an atrial lead 24 and a ventricular lead 26. The system 20 may also include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

The system 20, as shown in FIG. 1, is implanted in a human body 28 with portions of the atrial and ventricular leads 24 and 26 inserted into a heart 30 to detect and analyze electric cardiac signals produced by both the atria 32 and the ventricles 34 of the heart 30. The atrial and ventricular leads 24 and 26 also provide electrical energy to the heart 30 under certain predetermined conditions to treat various types of cardiac arrhythmia, including, for example, atrial and ventricular tachycardias, and atrial and ventricular fibrillation of the heart 30.

Figure 2:
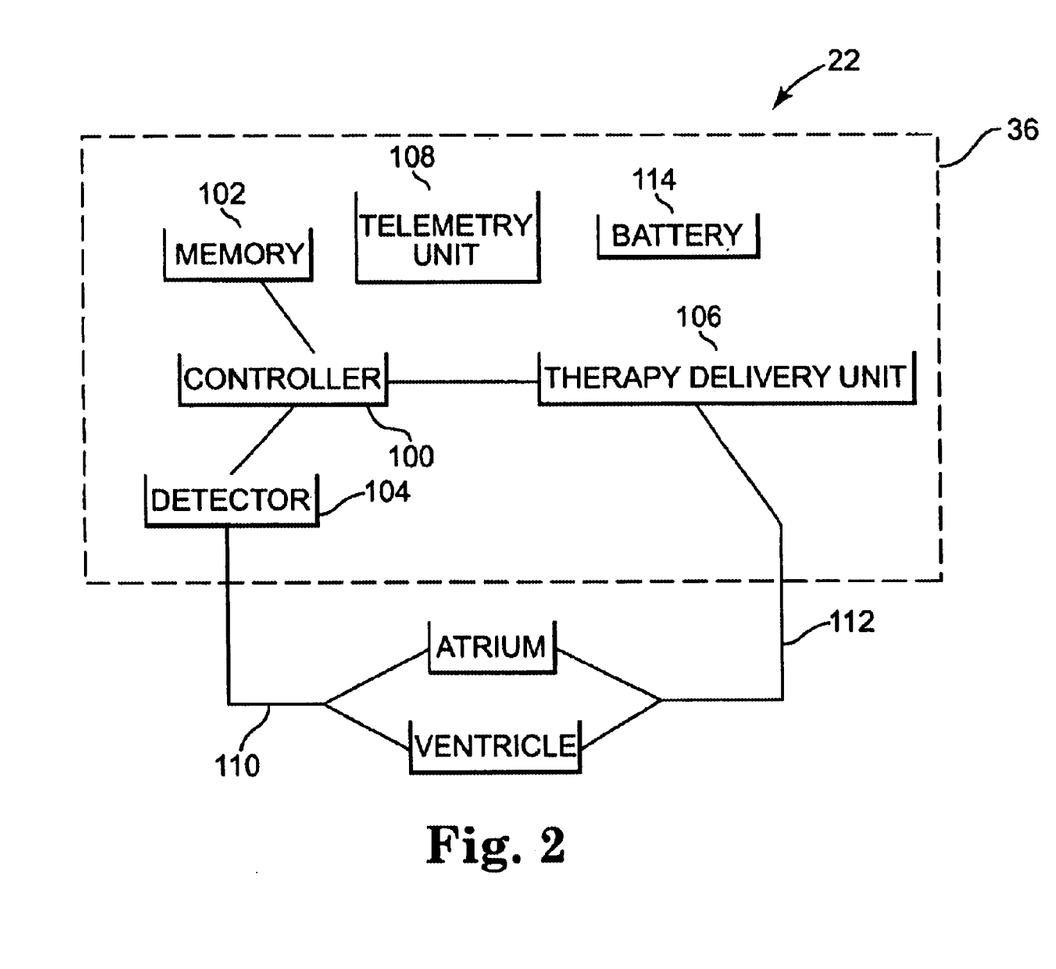
FIG. 2 is a block diagram of several components housed in the implantable medical device of FIG. 1.

A block diagram of the implantable pulse generator 22 electronics is provided in FIG. 2. The implantable pulse generator 22 includes a housing 36 which contains, among other components, a controller 100 and memory 102, which typically includes read only memory (ROM) and random access memory (RAM). Pulse generator 22 further includes a detector 104, which includes atrial and ventricular sense amplifiers (not shown), a therapy delivery unit 106, and a telemetry unit 108. The electronic components of the pulse generator 22 are interconnected by way of a bus connection (not shown).

Power to the implantable pulse generator 22 is supplied by an electrochemical battery 114 which is contained within the implantable pulse generator housing 36. The implantable pulse generator 22 is interrogated and programmed via bi-directional radio frequency telemetry through cooperative operation between the telemetry unit 108 and an external programmer in a manner known in the art.

The atrial therapy inhibiting methodologies implemented by system 20 are embodied in one or more algorithms as firmware within memory 102, and are executed by the controller 100. The detector 104 is also connected to the controller 100, and contains a plurality of electrical connections 110 coupled to the atrial and ventricular sense amplifiers. The outputs of the sense amplifiers are connected to the controller 100, such that atrial and ventricular signals received through the detector 104 are analyzed by the algorithms implemented within the controller 100. The controller 100 is also coupled to the therapy delivery unit 106, which controls the delivery of electrical energy to the heart 30 through a plurality of electrical output connections 112 to affect the sinus rhythm of the heart 30 under certain combinations of atrial 32 and ventricular 34 conditions.

Referring again to FIG. 1, a connector block 38 is mounted on the implantable pulse generator 22. The connector block 38 has two connector ports for coupling the atrial lead 24 and the ventricular lead 26 to the detector 104 and the therapy delivery unit 106 of the implantable pulse generator 22. Additional connector ports can be added to the connector block 38, as in the case of configurations having three or more ports as is known in the art. Alternatively, the connector block 38 can be provided with one connector port for coupling an implantable transvenous lead to the implantable pulse generator 22. It is understood that atrial and ventricular sensing and pacing/defibrillating functions may be accomplished using a single lead system employing atrial and ventricular conductors/electrodes, rather than by use of the dual lead system shown in FIG. 1.

In general, the electrical activity in the heart 30 is sensed, and therapies are delivered to the heart 30, through at least one transvenous pacing/defibrillation lead connected to the implantable pulse generator 22. Unipolar and/or bipolar pacing and sensing electrodes can be used in conjunction with the transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for purposes of determining atrial intervals. Ventricular activity is monitored by sensing for the occurrence of ventricular R-waves for purposes of determining ventricular intervals. Pacing therapies to the atrium 32 or ventricle 34 are delivered to the heart 30 using these same leads.

The system 20 may also employ defibrillation electrodes which are connected to the electrical output connections 112, and serve to deliver cardioversion and defibrillation level electrical pulses to the heart 30 as determined by the programming of controller 100. The housing 36 of the system 20 may be used as an optional defibrillation electrode, where the housing 36 of the implantable pulse generator 22 is electrically connected to a cathode pole of the therapy delivery unit 106. All defibrillation electrical pulses are delivered to the heart with at least two defibrillation electrodes, or through at least one defibrillation electrode and the housing 36 of the implantable pulse generator 22. The system 20 supports a plurality of pacing regimens.

In addition to the lead configuration shown in FIG. 1, the system 20 supports several other lead configurations and types. For example, it is possible to use ventricular epicardial rate sensing, atrial endocardial bipolar pace/sensing, ventricular endocardial bipolar pace/sensing, epicardial patches, and ancillary leads in conjunction with the implantable pulse generator 22.

In the embodiment of system 20 depicted in FIG. 1, the atrial lead 24 has an elongated body 40 having a peripheral surface 42, proximal and distal ends, 44 and 46, a first atrial electrode 48, and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongated body 40.

The first atrial electrode 48 is situated at or adjacent to the distal end 46 of the elongated body 40 and is either a pacing tip electrode or a semi-annular or annular electrode partially or completely encircling the peripheral surface 42 of the elongated body 40. The second electrode 50 is an annular or semi-annular electrode encircling or partially encircling the peripheral surface 42 of the elongated body 40. The second electrode 50 is spaced longitudinally along the peripheral surface 40 from the first atrial electrode 48 and the distal end 46 of the atrial lead 24, such that when the atrial lead 24 is inserted into the right atrial chamber 52 of the heart 30, the first atrial electrode 48 is in physical contact with a portion of a wall of the right atrial chamber 52 of the heart 30 and the second electrode 50 is within the right atrium chamber 52.

Electrical conductors extend longitudinally within the elongated body 40 of the atrial lead 24 from a connection end at the proximal end 44 and make connection to the first and second atrial electrodes 48 and 50. The proximal end 44 of the atrial pacing lead 24 is attached to the connector block 38 of the implantable pulse generator 22. The connector block 38 provides electrical coupling between the contact ends of the electrical conductors of atrial lead 24 with the atrial sense amplifier of the detector 104 and the therapy delivery unit 106, such that the implantable pulse generator 22 receives bipolar signals from, and delivers bipolar pacing to, the right atrium 52 of the heart 30.

The ventricular lead 26 includes an elongated body 54 having a peripheral surface 56, proximal and distal ends, 58 and 60, and a ventricle pacing electrode 62. The ventricular lead 26 also includes a first defibrillation electrode 64 and a second defibrillation electrode 66 situated on the peripheral surface 56 of the elongated body 54. The ventricular pacing electrode 62 and the first defibrillation electrode 64 are adapted to receive electrical cardiac signals from the right ventricle chamber 68 of the heart 30, and are attached on the peripheral surface of the elongated body 54. The second defibrillation electrode 66 is spaced apart and longitudinally on the peripheral surface 56 of the ventricular lead 26. This configuration affords positioning of the ventricular lead 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to right atrium.

Electrical leads extend longitudinally within the elongated body 54 of the ventricular lead 26 from a connection end at the proximal end 58 to make connection with the ventricular pacing electrode 62, the first defibrillation electrode 64, and the second defibrillation electrode 66. The proximal end 58 of the ventricular lead 26 is attached to the connector block 38 of the implantable pulse generator 22. The connector block 38 provides for electrical coupling between the contact ends of the electrical conductors of ventricular lead 26 with the ventricular sense amplifier of the detector 104 and the therapy delivery unit 106, such that the implantable pulse generator 22 receives either unipolar or bipolar signals from, and can deliver unipolar or bipolar pacing to, the right ventricle 68 and defibrillation electrical pulses to the ventricles 34 of the heart 30.

The atrial lead 24 and the ventricular lead 26 are attached to, and are separated from, the implantable pulse generator 22 to facilitate insertion of the atrial lead 24 into the heart 30. The proximal end 44 of the atrial lead 24 and the proximal end 58 of the ventricular lead 26 are adapted to seal together with the connector ports of the implantable pulse generator 22 to thereby engage the contact ends of the atrial lead 24 and the ventricular lead 26 with the plurality of electrical connections 110 and the therapy delivery unit 106 of the implantable pulse generator 22. The implantable pulse generator 22 of the system 20 is then positioned subcutaneously within the body 28.

Figure 3:
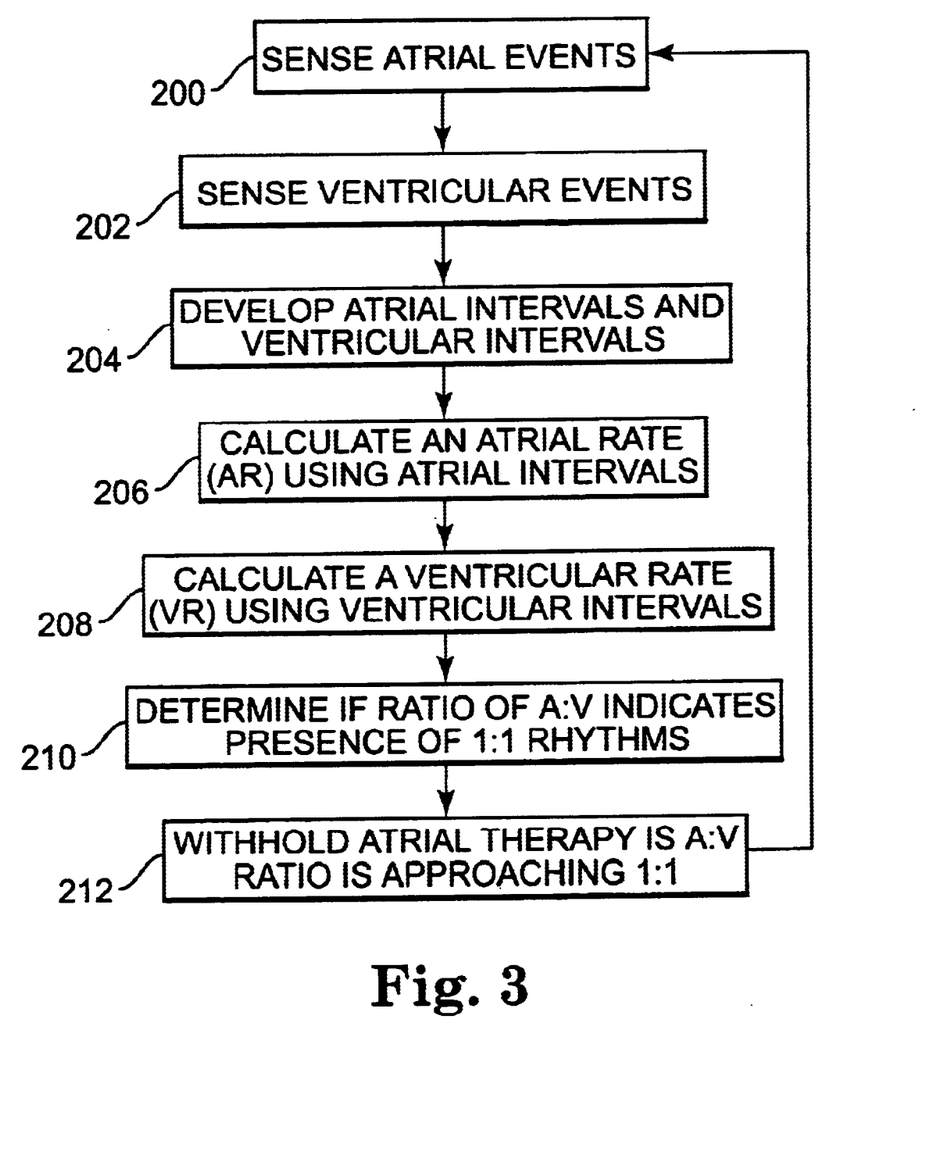
FIG. 3 is a flow chart depicting various processes of an atrial therapy inhibiting methodology in accordance with an embodiment of the present invention.

Referring now to FIG. 3, there is shown in flow diagram form several processes of an atrial therapy inhibiting methodology implemented by system 20 in accordance with an embodiment of the present invention. An atrial therapy inhibiting methodology of the present invention evaluates a series of atrial intervals and ventricular intervals to ensure that atrial therapy, although indicated as potentially being needed or appropriate by the evaluation, is inhibited or withheld under certain conditions.

One condition of particular concern involves an increase in the rate of both atrial and ventricular events at approximately the same rate, such as occurs during exercise. In such a case, the ratio of atrial intervals relative to ventricular intervals (A:V) is normally about 1:1, notwithstanding the increased atrial and ventricular event rate.

In cases in which A:V ratios of about 1:1 are detected, it has been determined that atrial therapy should be inhibited or withheld. In one embodiment, for example, if the atrial rate fails to exceed the ventricular rate by a predetermined factor, referred to herein as a bias factor, atrial therapy is inhibited. The atrial detection enhancement of the present invention may thus be viewed as a "detection inhibitor."

Detection and response decisions made by the system 20 are based on detected cardiac events and computed event intervals. As is shown in FIG. 3, atrial and ventricular events are detected 200, 202 from which atrial and ventricular intervals are developed 204 in a manner known in the art.

Detection 200 of atrial events typically involves sensing of atrial P-waves. An atrial interval (e.g., an A—A wave time interval) is computed 204 using the detected atrial P-waves. In a similar manner, detection 202 of ventricular events typically involves sensing of ventricular R-waves. A ventricular interval (e.g., an R—R wave time interval) is computed 204 using the detected ventricular R-waves.

An atrial rate (AR) is calculated 206 using the computed atrial intervals. A ventricular rate (VR) is calculated 208 using the computed ventricular intervals. The atrial and ventricular rates are evaluated to determine if the atrial and ventricular rhythms are approximately equal. In one embodiment, a ratio of atrial rates relative to ventricular rates is computed. If this AR:VR ratio indicates 210 the presence of a 1:1 rhythm condition, any atrial therapy that may otherwise appear to be appropriate under present conditions is withheld 212.

If the AR:VR ratio indicates 210 that a 1:1 rhythm condition is not present, and further that the atrial rate exceeds the ventricular rate by a selected bias factor, then an atrial therapy that may be appropriate under present conditions is not withheld (i.e., not inhibited). In this scenario, other atrial detection procedures, if enabled, are typically invoked to determine if atrial therapy should be delivered or withheld, or which atrial therapy should be delivered.

By way of example, a dual atrial and ventricular windowing methodology for detecting and verifying atrial arrhythmias is disclosed in commonly-owned U.S. patent application 09/827,769 filed Apr. 6, 2001 entitled "Atrial and Ventricular Tachyarrhythmia Detection System and Method," now U.S. Pat. No. 6,658,286, which is hereby incorporated herein by reference. This or other known atrial arrhythmia detection methodologies may be employed in combination with the present invention to determine if and when atrial therapy should be delivered or withheld, or which atrial therapy should be delivered.

Figure 4:
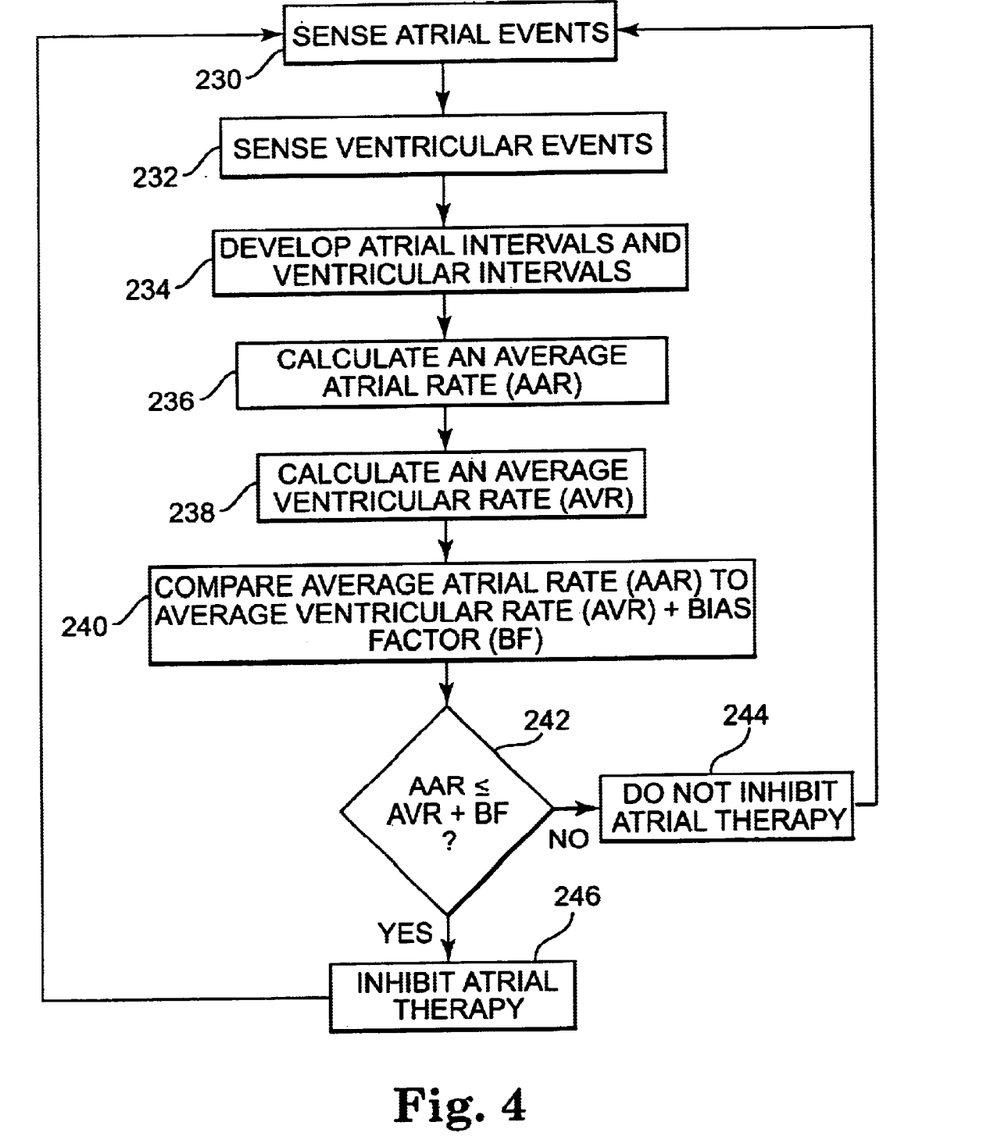
FIG. 4 is a flow chart depicting various processes of an atrial therapy inhibiting methodology in accordance with another embodiment of the present invention.

FIG. 4 illustrates in flow diagram form several processes of an atrial therapy inhibiting methodology implemented by system 20 in accordance with another embodiment of the present invention. As in the previously discussed illustrative embodiment, detection and response decisions made by the system 20 are based on detected cardiac events and computed event intervals. In particular, atrial and ventricular events are detected 230, 232 from which atrial and ventricular intervals are developed 234.

In accordance with this embodiment, an average atrial rate (AAR) is calculated 236 using a set of the computed atrial intervals. The number of atrial intervals used to calculate the average atrial rate may range between about 4 and 60 of the most recent atrial intervals, with a preferred range being between about 5 and 20 of the most recent atrial intervals. For example, the number of atrial intervals used to calculate the average atrial rate may be a number up to about 10 of the most recent atrial intervals. An average atrial rate is computed by employing a known averaging algorithm, which is applied to this set of n most recent atrial intervals.

An average ventricular rate (AVR) is calculated 238 using a set of the computed ventricular intervals. The number of ventricular intervals used to calculate the average ventricular rate may range between about 4 and 60 of the most recent ventricular intervals, with a preferred range being between about 5 and 20 of the most recent ventricular intervals. For example, the number of ventricular intervals used to calculate the average ventricular rate may be a number up to about 10 of the most recent ventricular intervals. An average ventricular rate is computed using a known averaging algorithm operating on this set of m most recent ventricular intervals.

In one approach, an equal number of interval samples are used to calculate the respective average atrial and ventricular interval rates (i.e., n=m). For example, 10 of the most recent atrial and ventricular intervals can be used to calculate the respective average atrial and ventricular interval rates. In an alternative approach, the number of interval samples used to calculate the respective average atrial and ventricular interval rates may differ. For example, a set of n most recent atrial interval samples can be used to calculate the average atrial interval rate, while a set of m most recent ventricular atrial interval samples can be used to calculate the average ventricular interval rate, where n and m represent different integers (e.g., n=15 and m=10 or n=12 and m=8, for example).

According to an alternative approach, average atrial and ventricular rates are developed based on a number of atrial and ventricular intervals respectively computed during a predetermined snapshot of time, rather than being based on a number n, m of the most recent atrial and ventricular intervals. The predetermined snapshot duration may range between about 2 seconds and 60 seconds, with a preferred range being between about 4 seconds and 30 seconds.

For example, the average atrial rate may be computed based on a number n of atrial intervals computed during the last x seconds (e.g., a snapshot of atrial intervals computed the during the last x=15 seconds). The average ventricular rate may be computed based on a number m of ventricular intervals computed during the last y seconds, where the time durations x and y are typically the same, but may be different (e.g., a snapshot of ventricular intervals computed the during the last y=15 seconds). The relationship (e.g., ratio) between average atrial and ventricular rates is developed using the number n, m of respective atrial and ventricular intervals captured during the predefined snapshot duration.

In accordance with a further embodiment, the average atrial and ventricular rates are developed based on atrial and ventricular time durations associated with detection of a predetermined number of the most recent atrial and ventricular intervals. For example, an atrial time duration, x, is determined as the amount of time associated with detection of the most recent n atrial intervals. A ventricular time duration, y, is determined as the amount of time associated with detection of the most recent m ventricular intervals.

The relationship (e.g., ratio) between average atrial and ventricular rates is developed using the atrial and ventricular time durations, y and x.

The average atrial and ventricular rates are used, together with a bias factor (BF), in the process of determining whether to inhibit atrial therapy under present conditions. The bias factor, BF, is a programmable value that can be adjusted based on a desired level of sensitivity or insensitivity to detection of differences between atrial and ventricular rates. For example, adjusting the bias factor, BF, effectively adjusts a threshold that demarcates the ratio of the average atrial and ventricular rates (i.e., AAR:AAV) from a 1:1 AAR to AVR ratio. In other words, the bias factor, BF, may be adjusted so that the atrial tachyarrhythmia detection enhancement of the present invention is less sensitive to potential atrial oversensing and undersensing.

As is further shown in FIG. 4, the average atrial rate is compared 240 to the average ventricular rate plus the predetermined bias factor. In formulaic terms, the value of AAR is compared to the value of AVR+BF. If 242 the average atrial rate is less than or equal to the average ventricular rate plus the predetermined bias factor (i.e., if AAR≦AVR+BF), then atrial therapy is inhibited 246. In this case, the present MR to AVR ratio has exceeded the preestablished AAR to AVR ratio threshold. In other words, the system 20, under these conditions, has detected an AAR to AVR ratio that is undesirably close to a 1:1 rhythm condition.

Atrial therapy is not inhibited 244 (e.g., is enabled for invocation) if the average atrial rate is greater than the average ventricular rate plus the predetermined bias factor (i.e., if AAR>AVR+BF). Under conditions in which atrial therapy is not inhibited 244, other atrial detection procedures, if enabled, are typically invoked to determine if atrial therapy should ultimately be delivered or withheld, or which atrial therapy should be delivered.

Figure 6:
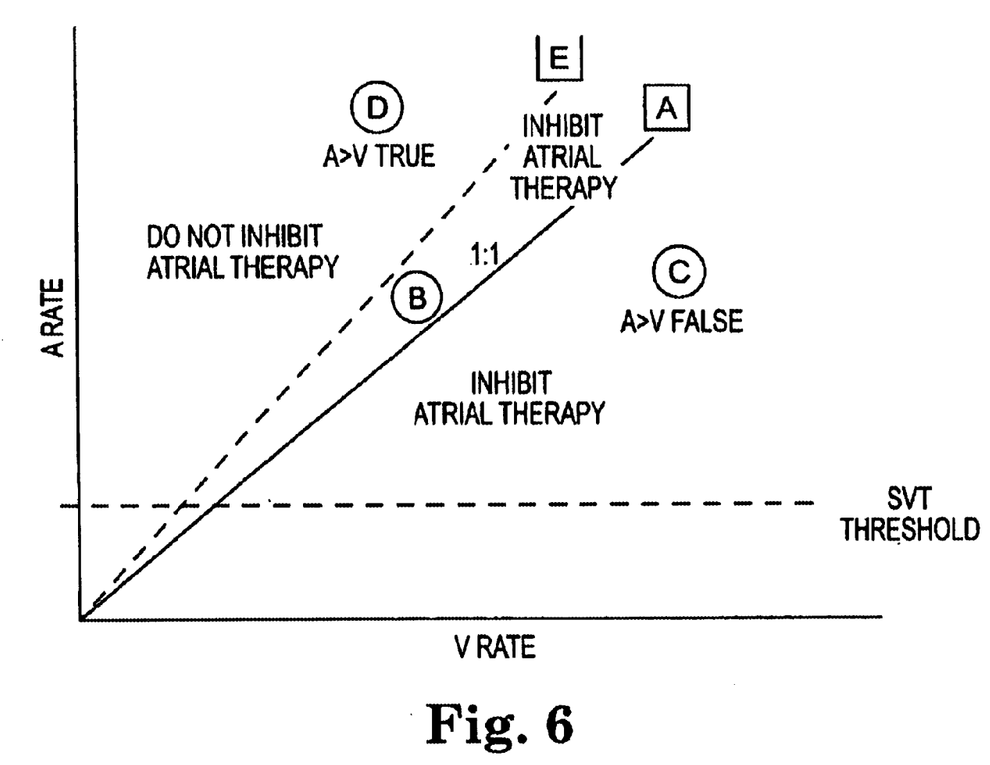
FIG. 6 is a graphical depiction of a detection window that differentiates AAR/AVR ratios for which atrial thereby is or is not inhibited as a function of a predetermined bias factor.

FIG. 6 graphically illustrates the effect of the bias factor, BF, on detection sensitivity or insensitivity to differences between average atrial and ventricular rates. The graph of FIG. 6 has an x axis representing increasing average ventricular rates (V Rate) and a y axis representing increasing average atrial rates (A Rates). The line identified by label A represents equivalency between average atrial and ventricular rates (i.e., a 1:1 AAR to AVR ratio or a 1:1 rhythm condition).

As the average atrial rate increases relative to the average ventricular rate, as is the case in region B in FIG. 6, the ratio of AAR to AVR increases above the 1:1 AAR/AVR ratio. The region B, defined between lines A and E, depicts a bias factor window. The bias factor window defines a region B in which atrial therapy is either inhibited or not inhibited for ratios of AAR to AVR that exceed 1:1 above a predefined threshold, such as a predefined SVT threshold or other atrial arrhythmia threshold.

For ratios of AAR to AVR falling in region C, and assuming that the SVT or other atrial arrhythmia threshold is exceeded, the average atrial rate does not exceed the average ventricular rate. As such, atrial therapy is inhibited for ratios of AAR to AVR falling in region C.

For ratios of AAR to AVR falling in region D, and assuming that the SVT other atrial arrhythmia threshold is exceeded, the average atrial rate exceeds the average ventricular rate by at least the predetermined bias factor, BF. As such, atrial therapy is not inhibited for ratios of AAR to AVR falling in region D. In this case, the AAR to AVR ratio is sufficiently distant from the 1:1 AAR/AVR ratio.

However, for ratios of AAR to AVR falling in region B, and again assuming that the SVT other atrial arrhythmia threshold is exceeded, the average atrial rate does not exceed the average ventricular rate by at least the predetermined bias factor, BF. In this case, an inhibit threshold, $I_{TH}$, which is represented as dashed line E in FIG. 6, has not been exceeded. The inhibit threshold, $I_{TH}$, can, for example, be characterized by the equation $I_{TH}=(AAR+BF)/AVR$. Accordingly, atrial therapy is inhibited for ratios of AAR to AVR falling in region B. In this case, the AAR to AVR ratio is not sufficiently distant from the 1:1 AAR/AVR ratio.

Figure 5:
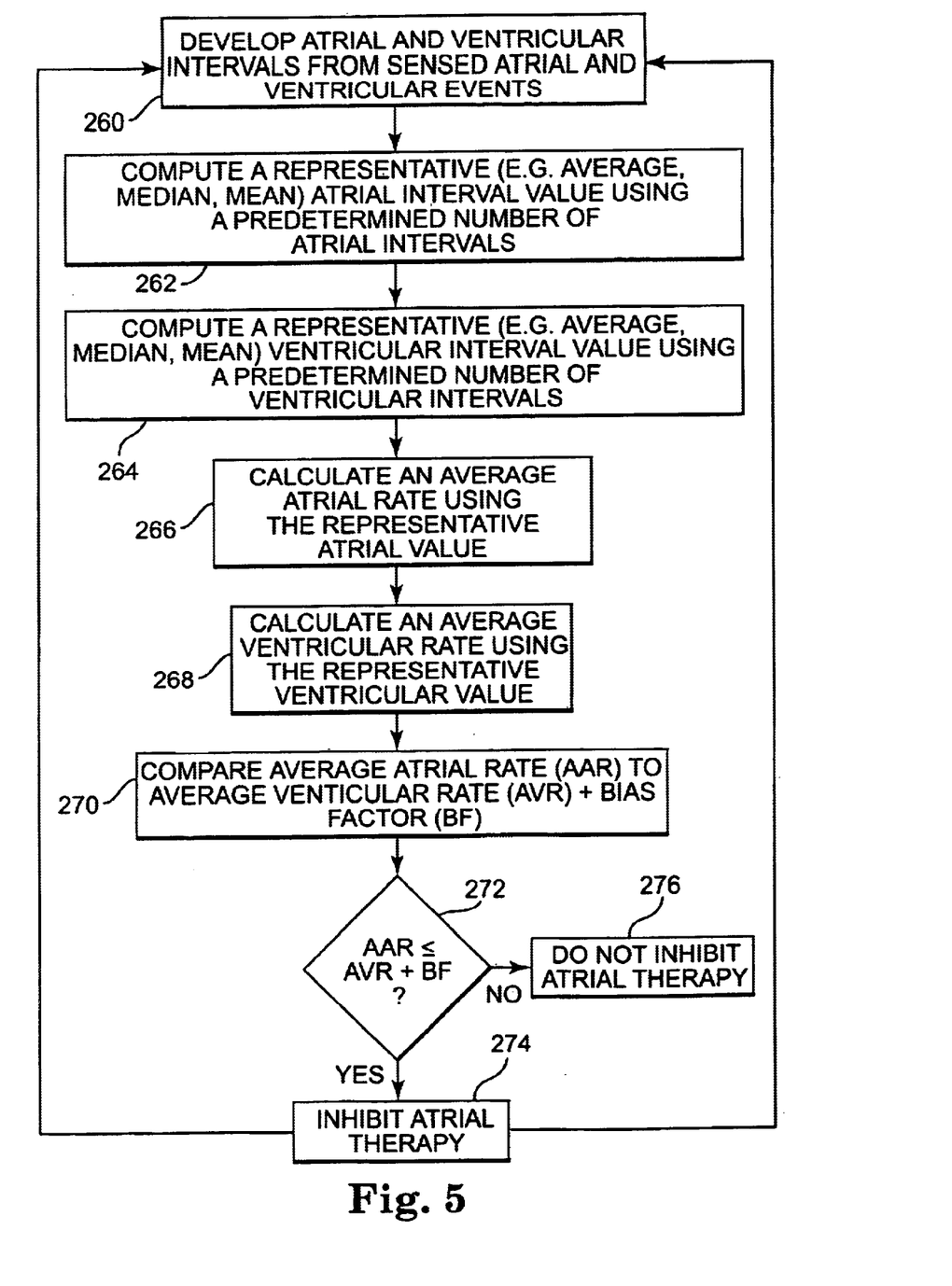
FIG. 5 is a flow chart depicting various processes of an atrial therapy inhibiting methodology in accordance with a further embodiment of the present invention.

FIG. 5 illustrates several processes of an atrial therapy inhibiting methodology implemented by system 20 in accordance with a further embodiment of the present invention. As in the previously discussed illustrative embodiments, detection and response decisions made by the system 20 are based on detected cardiac events and computed event intervals. Atrial and ventricular events are detected from which atrial and ventricular intervals are developed 260.

In accordance with this embodiment, a "representative" atrial interval rate is computed 262 using a predetermined number of atrial interval samples. The predetermined number of atrial intervals used to calculate the representative atrial interval rate may range between 4 and 60 of the most recent atrial intervals, with between 5 and 20 of the most recent atrial intervals representing a preferred range, and 10 of the most recent atrial intervals representing a suitable sampling within this preferred range.

The representative atrial interval rate, in one embodiment, represents an "average" of the set of n most recent atrial interval samples. Various types of averaging algorithms can be employed. For example, the representative atrial interval rate can be computed by determining the arithmetic or weighted average of the set of n most recent atrial interval samples. Alternatively, the representative atrial interval rate may be computed as the mean of the set of n most recent atrial interval samples. The representative atrial interval rate may, for example, represent the arithmetic mean, geometric mean or harmonic mean of the set of n most recent atrial interval samples.

The representative atrial interval rate may alternatively be computed as the median of the set of n most recent atrial interval samples. Also, averaging techniques that employ standard deviation computations may also be used to compute the representative atrial interval rate, such as those employing one, two or three sigma computations for excluding statistically aberrant atrial interval rate samples from consideration. Averaging techniques that exclude the longest, shortest, or both longest and shortest of the set of n most recent atrial interval samples may also be employed.

A "representative" ventricular interval rate is computed 264 using a predetermined number of ventricular interval samples. The predetermined number of ventricular intervals used to calculate the representative ventricular interval rate may range between about 5 and 20 of the most recent ventricular intervals, with 10 of the most recent ventricular intervals representing a suitable sampling. The predetermined number of ventricular and atrial intervals used to respectively compute the representative ventricular and atrial interval rates may represent the same or different number of samples.

The representative ventricular interval rate represents an "average" of the set of m most recent ventricular interval samples. The representative ventricular interval rate can, for example, be computed using the approaches described above with respect to computing a representative atrial interval rate.

An average atrial rate is calculated 266 using the representative atrial interval rate. The average atrial rate, according to this illustrative embodiment, is preferably expressed in terms of beats per minute (bpm). In this case, the representative atrial interval rate is converted to an average atrial rate expressed in terms of beats per minute using known techniques.

An average ventricular rate is calculated 268 using the representative ventricular interval rate. The average ventricular rate, according to this illustrative embodiment, is converted to an average ventricular rate expressed in terms of beats per minute using known techniques.

The calculated average atrial and ventricular rates are used, together with a predetermined bias factor, to determine whether or not to inhibit atrial therapy. The value of the bias factor, BF, is programmable in the ranges of 5–30 bpm, where 20 bpm is an appropriate number. The average atrial rate is compared 270 to the average ventricular rate plus the predetermined bias factor. In other words, the value of AAR is compared to the value of AVR+BF. If 272 the average atrial rate is less than or equal to the average ventricular rate plus the predetermined bias factor (i.e., if AAR≦AVR+BF), then atrial therapy is inhibited 274.

Atrial therapy is not inhibited 276 if the average atrial rate is greater than the average ventricular rate plus the predetermined bias factor (i.e., if AAR>AVR+BF). As was discussed previously, other atrial detection procedures are typically invoked to determine if atrial therapy should ultimately be delivered or withheld, or which atrial therapy should be delivered.

The predetermined bias factor, BF, may be expressed in various forms. In the illustrative embodiment described above, for example, the predetermined bias factor, BF, is expressed in terms of a specified number of beats per minute, such as 20 beats per minute. The predetermined bias factor, BF, may alternatively be expressed in terms of percentages. For example, the predetermined bias factor, BF, may be programmed to represent a percentage between 105 and 125 percent. Atrial therapy can be inhibited, for example, if the average atrial rate fails to exceed the average ventricular rate by at least the predetermined percentage, such as by at least 115 percent.

The atrial therapy inhibiting methodology of the present invention may be employed in a detection approach that utilizes rate zone detection algorithms. In accordance with a further embodiment of the present invention, the system 20 can be programmed to define a number of different rate zones for classifying atrial and ventricular interval rates. The number of atrial and ventricular rate zones typically differ, but may be the same. For example, ventricular interval rates may be classified using one, two or three ventricular rate zones. Atrial interval rates are typically classified using one or two atrial rate zones.

In general, a number of rate zones are defined to classify atrial and ventricular interval rates that are above a defined upper limit for normal atrial and ventricular interval rates, respectively. A rate zone is a range of atrial or ventricular interval rates that has an associated lower rate threshold. Typically, a given rate zone is defined by its lower rate threshold and that of an adjacent rate zone (e.g., next higher rate zone). For each rate zone, the lower rate threshold is a programmable value in beats per minute (bpm) and is the value to which the system 20 compares each sensed atrial or ventricular interval rate in order to determine the zone in which that atrial or ventricular interval rate belongs.

In one embodiment, ventricular rate zones can be defined for slow ventricular tachycardia (VT-1), fast ventricular tachycardia (VT), and ventricular fibrillation (VF). Atrial rate zones can be defined to classify supraventricular tachycardia (SVT) and atrial fibrillation (AF). The lower rate threshold for each of the atrial and ventricular rate zones may be programmed at a given beat-per-minute as is appropriate.

According to one approach, to determine if an individual atrial or ventricular interval rate falls into a particular programmed rate zone, the system 20 detects the intervals between a series of the most recent consecutive atrial P-waves or ventricular R-waves. Detecting the intervals between 40 of the most recent consecutive atrial P-waves and 10 of the most recent consecutive ventricular R-waves, for example, is considered to be a good sampling.

These atrial and ventricular samplings may be referred to as detection windows, with a new atrial and ventricular detection window occurring with each consecutive atrial P-wave and ventricular R-wave, respectively. The lengths of the atrial and ventricular detection windows, in the above example, are 40 and 10 samples, respectively. The length of the atrial and ventricular windows may be varied, such as between 20–60 and 5–15 samples, for example.

The system assesses the atrial and ventricular intervals in relation to one or more of the predefined atrial and ventricular rate zones, respectively. The use of atrial and ventricular detection windows helps to differentiate and classify atrial and ventricular tachyarrhythmias into a predefined rate zone, and helps to ensure that the correct atrial or ventricular therapy is delivered to the patient.

The atrial therapy inhibiting methodologies of the present invention may be implemented for each of the predefined rate zones according to this embodiment. For example, the atrial therapy inhibiting methodologies of the present invention may be implemented in the context of various types of atrial or ventricular tachyarrhythmia detection processes, including those that employ rate zone differentiation, such as those disclosed in commonly owned U.S. Pat. No. 5,978,707 and U.S. patent application Ser. No. 09/827,769 entitled "Atrial and Ventricular Tachyarrhythmia Detection System and Method," filed Apr. 6, 2001, now U.S. Pat. No. 6,658,286, both of which are hereby incorporated herein by reference in their respective entireties.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of inhibiting delivery of atrial therapy, comprising:

developing atrial intervals and ventricular intervals from sensed atrial and ventricular events, respectively;

computing a representative atrial interval rate and a representative ventricular interval rate using a predetermined number of the atrial and ventricular intervals, respectively;

calculating an average atrial rate and an average ventricular rate using the representative atrial and ventricular interval rates, respectively; and inhibiting delivery of atrial therapy if the average atrial rate exceeds an atrial arrhythmia threshold and the average atrial rate fails to exceed the average ventricular rate by at least a predetermined factor.

2. The method of claim 1, wherein calculating the average atrial and ventricular rates comprises calculating the average atrial and ventricular rates on a beat per minute basis using the representative atrial and ventricular interval rates.

3. The method of claim 1, wherein the predetermined number of the atrial and ventricular intervals is between 4 and 60 of the most recent atrial and ventricular intervals, respectively.

4. The method of claim 1, wherein the predetermined number of the atrial and ventricular intervals is about 10, respectively.

5. The method of claim 1, wherein the predetermined factor is at least 105 percent.

6. The method of claim 1, wherein:
calculating the average atrial and ventricular rates further comprises calculating the average atrial and ventricular rates on a beat per minute basis using the representative atrial and ventricular interval rates; and
the predetermined factor is between 10 and 30 beats per minute.

7. The method of claim 1, wherein:
calculating the average atrial and ventricular rates further comprises calculating the average atrial and ventricular rates on a beat per minute basis using the representative atrial and ventricular interval rates; and
the predetermined factor is about 20 beats per minute.

8. The method of claim 1, wherein the representative atrial and ventricular interval rates are computed by computing an average of the predetermined number of the atrial and ventricular intervals, respectively.

9. The method of claim 1, wherein the representative atrial and ventricular interval rates are computed by computing a median of the predetermined number of the atrial and ventricular intervals, respectively.

10. The method of claim 1, wherein the representative atrial and ventricular interval rates are computed by computing a mean of the predetermined number of the atrial and ventricular intervals, respectively.

11. The method of claim 1, further comprising enabling delivery of atrial therapy if the average atrial rate exceeds the average ventricular rate by at least the predetermined factor.

12. A method of inhibiting delivery of atrial therapy, comprising:
developing atrial intervals and ventricular intervals from sensed atrial and ventricular events, respectively;
calculating an average atrial rate and an average ventricular rate developed from a predetermined number of the atrial and ventricular intervals, respectively; and
inhibiting delivery of atrial therapy if the average atrial rate exceeds an atrial arrhythmia threshold and the average atrial rate fails to exceed the average ventricular rate by at least a predetermined factor.

13. The method of claim 12, wherein calculating the average atrial and ventricular rates further comprises calculating the average atrial and ventricular rates on a beat per minute basis using an average of the predetermined number of the atrial and ventricular intervals, respectively.

14. The method of claim 12, wherein calculating the average atrial and ventricular rates further comprises calculating the average atrial and ventricular rates on a beat per minute basis using a median of the predetermined number of the atrial and ventricular intervals, respectively.

15. The method of claim 12, wherein calculating the average atrial and ventricular rates further comprises calculating the average atrial and ventricular rates on a beat per minute basis using a mean of the predetermined number of the atrial and ventricular intervals, respectively.

16. The method of claim 12, wherein calculating the average atrial and ventricular rates comprises calculating the average atrial and ventricular rates using a number n of the atrial intervals and a number m of the ventricular intervals developed during a predetermined time period.

17. The method of claim 12, wherein calculating the average atrial and ventricular rates comprises calculating the average atrial and ventricular rates using a first time period during which a number n of the atrial intervals is developed and a second time period during which a number m of the ventricular intervals is developed.

18. The method of claim 12, wherein the predetermined number of the atrial and ventricular intervals is between 4 and 60 of the most recent atrial and ventricular intervals, respectively.

19. The method of claim 12, wherein the predetermined number of the atrial and ventricular intervals is about 10, respectively.

20. The method of claim 12, wherein the predetermined factor is at least 105 percent.

21. The method of claim 12, wherein:
calculating the average atrial and ventricular rates further comprises calculating the average atrial and ventricular rates on a beat per minute basis using an average of the predetermined number of the atrial and ventricular intervals; and
the predetermined factor is between 10 and 30 beats per minute.

22. The method of claim 12, wherein:
calculating the average atrial and ventricular rates further comprises calculating the average atrial and ventricular rates on a beat per minute basis using an average of the predetermined number of the atrial and ventricular intervals; and
the predetermined factor is about 20 beats per minute.

23. The method of claim 12, further comprising enabling delivery of atrial therapy if the average atrial rate exceeds the average ventricular rate by at least the predetermined factor.

24. A body implantable system, comprising:
at least one lead comprising atrial and ventricular electrodes;
a detector, coupled to the at least one lead, that senses atrial events and ventricular events; and
a control circuit coupled to the detector, the control circuit calculating an average atrial rate and an average ventricular rate developed from a predetermined number of the atrial and ventricular intervals, respectively, the control circuit inhibiting delivery of atrial therapy if the average atrial rate exceeds an atrial arrhythmia threshold and the average atrial rate fails to exceed the average ventricular rate by at least a predetermined factor.

25. The system of claim 24, wherein the control circuit calculates the average atrial and ventricular rates on a beat per minute basis using an average of the predetermined number of the atrial and ventricular intervals, respectively.

26. The system of claim 24, wherein the control circuit calculates the average atrial and ventricular rates on a beat per minute basis using a median of the predetermined number of the atrial and ventricular intervals, respectively.

27. The system of claim 24, wherein the control circuit calculates the average atrial and ventricular rates on a beat per minute basis using a mean of the predetermined number of the atrial and ventricular intervals, respectively.

28. The system of claim 24, wherein predetermined number of the atrial and ventricular intervals is between 4 and 60 of the most recent atrial and ventricular intervals, respectively.

29. The system of claim 24, wherein the predetermined number of the atrial and ventricular intervals is about 10, respectively.

30. The system of claim 24, wherein the predetermined factor is at least 105 percent.

31. The system of claim 24, wherein the control circuit calculates the average atrial and ventricular rates on a beat per minute basis using an average of the predetermined number of the atrial and ventricular intervals, and the predetermined factor is between 10 and 30 beats per minute.

32. The system of claim 24, wherein the control circuit calculates the average atrial and ventricular rates on a beat per minute basis using an average of the predetermined number of the atrial and ventricular intervals, and the predetermined factor is about 20 beats per minute.

33. The system of claim 24, wherein the control circuit enables delivery of atrial therapy if the average atrial rate exceeds the average ventricular rate by at least the predetermined factor.

34. A method of inhibiting delivery of atrial therapy, comprising:

developing atrial intervals and ventricular intervals from sensed atrial and ventricular events, respectively;

calculating an atrial rate and a ventricular rate developed from the atrial and ventricular intervals, respectively;

inhibiting delivery of atrial therapy if the atrial rate exceeds an atrial arrhythmia threshold and the average atrial rate fails to exceed the ventricular rate by at least a predetermined factor;

enabling atrial therapy delivery, subsequent to inhibiting atrial therapy delivery, if the atrial rate exceeds the ventricular rate by at least the predetermined factor; and delivering atrial therapy if atrial therapy delivery is enabled and at least one atrial arrhythmia detection process indicates atrial therapy delivery should be delivered.

35. The method of claim 34, wherein the at least one atrial arrhythmia detection process comprises:

developing atrial and ventricular interval rates from the sensed atrial and ventricular events, respectively;

classifying atrial interval rates in an atrial window, the atrial window having a first length and a first satisfaction criterion;

classifying ventricular interval rates in a ventricular window, the ventricular window having a second length and a second satisfaction criterion, the second length of the ventricular window differing from the first length of the atrial window to enhance detection of ventricular arrhythmias relative to atrial arrhythmia detection; and declaring an atrial episode in response to satisfying the atrial window by comparing classified atrial interval rates to the first satisfaction criterion.

36. The method of claim 35, wherein the first length of the atrial window is greater than the second length of the ventricular window.

37. The method of claim 35, further comprising verifying that the declared atrial episode is a sustained atrial episode in response to the atrial window being satisfied by a third satisfaction criterion for subsequent atrial interval rates.

38. The method of claim 34, wherein calculating the atrial and ventricular rates comprises calculating an average atrial rate and an average ventricular rate developed from the atrial and ventricular intervals, respectively.

39. The method of claim 34, wherein calculating the atrial and ventricular rates comprises calculating an average atrial rate and an average ventricular rate developed from a predetermined number of the atrial and ventricular intervals, respectively, further wherein the predetermined number of the atrial and ventricular intervals is between 4 and 60 of the most recent atrial and ventricular intervals, respectively.

40. The method of claim 34, wherein the predetermined factor is at least 105 percent.

41. The method of claim 34, wherein calculating the atrial and ventricular rates comprises calculating an average atrial rate and an average ventricular rate from the atrial and ventricular intervals, respectively, and the average atrial and ventricular rates are calculated on a beat per minute basis using an average, mean, or median of the atrial and ventricular intervals, respectively.

42. The method of claim 34, wherein calculating the atrial and ventricular rates further comprises calculating an average atrial rate and an average ventricular rate using a number n of the atrial intervals and a number m of the ventricular intervals developed during a predetermined time period.

* * * * *

UNITED STATES PATENT AND TRADEMARK OFFICE
CERTIFICATE OF CORRECTION

PATENT NO. : 6,904,319 B2
DATED : June 7, 2005
INVENTOR(S) : Seim et al.

It is certified that error appears in the above-identified patent and that said Letters Patent is hereby corrected as shown below:

Column 9,
Line 24, "present MR to AVR" should read -- present AAR to AVR --.

Signed and Sealed this

Twenty-ninth Day of November, 2005

JON W. DUDAS
*Director of the United States Patent and Trademark Office*